United States Patent [19]

Schole

[11] 4,175,120
[45] Nov. 20, 1979

[54] DENTIFRICE

[76] Inventor: Murray L. Schole, 487 Munroe Ave., North Tarrytown, N.Y. 10591

[21] Appl. No.: 956,200

[22] Filed: Oct. 30, 1978

[51] Int. Cl.$^2$ ............................ A61K 7/22; A61K 7/24
[52] U.S. Cl. ........................................ 424/54; 424/49; 424/55
[58] Field of Search .................................... 424/49–58

[56] References Cited
U.S. PATENT DOCUMENTS

| 1,633,336 | 6/1927 | Larson ..................................... 424/49 |
| 1,936,456 | 11/1933 | Larson et al. ........................... 424/55 |
| 3,122,483 | 2/1964 | Rosenthal ................................ 424/55 |
| 3,699,221 | 10/1972 | Schole et al. ........................... 424/54 |
| 4,130,638 | 12/1978 | Dhabhar et al. ........................ 424/55 |

*Primary Examiner*—Shep K. Rose
*Attorney, Agent, or Firm*—Brooks, Haidt, Haffner & Delahunty

[57] ABSTRACT

A dentifrice suitable for removing calculus and preventing the build-up of calculus on tooth enamel which contains strontium edetate and a ricinoleate, which have been found to provide a synergistic effect in both removal of calculus and prevention of its build-up.

3 Claims, No Drawings

DENTIFRICE

This invention relates to dental hygiene and, in particular, provides a dentifrice having valuable properties in the removal and prevention of calculus.

BACKGROUND OF THE INVENTION

It is known that water-containing dentifrices which include strontium and sequestering agents such as EDTA are effective in the treatment of hyper-sensitive dentin, gingivitis and periodontitis, apparently through the mechanism of substituting strontium for calcium in the calcium hydroxy apatite of the tooth (Schole et al U.S. Pat. No. 3,699,221 and 3,988,434).

It is also known that ricinoleic acid and various esters and salts which are surface active agents exhibit a higher contact angle with tooth enamel than other surface active agents.

SUMMARY OF THE INVENTION

In accordance with the present invention, a water-containing dentifrice including both strontium edatate and a ricinoleate provide a synergistic action in the removal of calculus from teeth and also in the prevention of its build-up.

It is understood by strontium edatate reference is made to the strontium chelate of EDTA and preferably the disodium strontium salt of ethylene diamine tetraacetic acid. When strontium edatate is present in an aqueous composition, the strontium is available in ionic form. Generally, the amount of strontium present in the dentifrice can be up to about 25 wt.% of strontium ion in the toothpaste, but much smaller amounts, as low as 2.5 wt.%, are effective. The strontium edatate can be formed in advance or can be prepared in the dentifrice as a mixture of a water soluble salt of EDTA together with a pharmacalogically innocuous water-soluble strontium salt, preferably in equivalents such that the pH will remain neutral.

The ricinoleate can be any of the alkali metal salts of ricinoleic acid (d-12-hydroxy-cis-9-octadecenoic acid), but preferably is the sodium salt. The amount of the ricinoleate is not particularly critical and can be as high as 10 wt.%. Amounts as low as 0.1 wt.% are, however, also effective.

The preferred proportions in the water-containing dentifrice are 10% by weight of strontium, calculated as disodium strontium ethylene diamine tetra acetate and 0.5% by weight of ricinoleate, calculated as the sodium salt.

The dentifrice product used should not include any calcium or other metal, salt or compound, from which any such metal would be sequestered by, and form the corresponding calcium or other metal chelate with the EDTA salt or chelate residue of the strontium chelate in the product.

In other words, the dentifrice products of the invention should not include any of the water-insoluble calcium, magnesium or aluminum compounds ordinarily incorporated as adjuvant bulk excipients in dentifrices, for example, as the abrasive ingredient, such as calcium carbonate, calcium pyrophosphate, magnesium oxide, aluminum oxide or hydroxide, and the like. So also, tin compounds, e.g., stannous fluoride and stannous chlorofluoride, likewise should be excluded.

In place of the foregoing water-insoluble bulk excipients for abrasive and other purposes, water-insoluble barium and strontium salts, for example, barium sulphate, barium carbonate, strontium carbonate and strontium phosphate can be used. The ricinoleate, being a surface-active wetting agent which is compatible with strontium, generally will obviate the need of other wetting agents.

The following are examples of several dentifrices in accordance with the invention.

EXAMPLE 1—TOOTHPASTE

| | | |
|---|---|---|
| Disodium Salt of Ethylenediamine Tetraacetic Acid | 20 | grams |
| Strontium Chloride (6H$_2$O) | 20 | grams |
| Strontium Carbonate | 25 | grams |
| Sodium Ricinoleate | 0.5 | grams |
| Algin | 1 | gram |
| Essential Oils (for flavoring) | 1 | gram |
| Propylene Glycol | 25 | grams |
| Alcohol | 0.9 | gram |
| Water quantity sufficient to make | 100 | grams |

EXAMPLE 2—TOOTHPASTE

| | | |
|---|---|---|
| Strontium Edatate | 30 | grams |
| Barium Sulfate | 30 | grams |
| Sodium Ricinoleate | 1.0 | gram |
| Algin | 1 | gram |
| Essential Oils (for flavoring) | 1 | gram |
| Propylene Glycol | 20 | grams |
| Alcohol | 0.9 | gram |
| Water quantity sufficient to make | 100 | grams |

EXAMPLE 3—TOOTHPASTE

| | | |
|---|---|---|
| Strontium Edatate | 8.0 | grams |
| Strontium Carbonate | 25.0 | grams |
| Methyl Salicylate | 1.25 | grams |
| Water | 33 | cc |
| Natrosol | 1.7 | grams |
| Sodium Ricinoleate | .1 | gram |
| Cpc | .3 | gram |
| Sodium Saccharin | 1.2 | grams |
| Propylene glycol | 25 | cc |
| Water sufficient to make | 100 | grams |

EXAMPLE 4-6—TOOTHPASTE

| | Preparation | | | |
|---|---|---|---|---|
| | 4 | 5 | 6 | |
| Strontium Edatate | 30 | 20 | 10 | grams |
| Strontium Carbonate | 25.0 | 25.0 | 25.0 | grams |
| Cetyl pyridinium chloride | 0.5 | 0.5 | 0.5 | gram |
| Oil of cassia | 0.75 | 0.75 | 0.75 | gram |
| Oil of wintergreen | 1.0 | 1.0 | 1.0 | gram |
| Propylene glycol | 25.0 | 25.0 | 25.0 | grams |
| Natrosol | 1.7 | 1.7 | 1.7 | grams |
| Saccharin | 1.2 | 1.2 | 1.2 | grams |
| Sodium Ricinoleate | 1.5 | .5 | .1 | grams |
| Water QSAD to 100 grams | | | | |

Strontium edatate is prepared by mixing equimolar amounts of strontium chloride hexahydrate and disodium ethylene diamine tetraacetic acid in hot distilled water, typically at 70° C., for a period of 20 minutes. The weight of strontium edatate is calculated as disodium strontium ethylene diamine tetraacetate and does not include the chloride present. As the ligand is formed, the two hydrogen ions are released for each molecule of Na$_2$ EDTA which results in a decrease of solution pH from about neutral to about 4, indicating the formation of the ligand. Strontium carbonate or other abrasive then is slowly added to the mixture and heating and mixing are continued as the strontium carbonate or other abrasive is mixed. When strontium carbonate is used, a reaction takes place with a visible evolution of carbon dioxide as the vapor. This reaction continues for about three to four hours at 70° C. The mixture is allowed to cool and additional ingredients such as propylene glycol and the like are added as well as make up water for that lost during the mixing of the strontium carbonate, Na$_2$ EDTA and strontium chloride. In Example 1, an excess of strontium chloride was utilized and hence this is separately stated. In Example 2, barium sulfate was substituted for strontium carbonate.

In a preferred alternate method of manufacture, Strontium edetate can be made by adding Strontium Carbonate to an aqueous solution of Disodium EDTA at a temperature 70° C.–80° C. The Strontium Carbonate is added slowly. At the completion of the reaction the pH will be between 7 and 8 which is adjusted by adding HC1. The bulk excipient or abrasive, such as Insoluble Metaphosphate (IMP) or Strontium Carbonate is added. The mixture is completed with the addition of Thickening Agent (Natrosol), Humectant (Sorbitol andGlycerine), Surfactant (Sodium Ricinoleate) and flavoring. EXAMPLE 7

| Liquid Dentrifice | | |
|---|---|---|
| Sodium Ricinoleate | 0.5 | gram |
| Glycerine | 20 | grams |
| Oil of cloves | 0.3 | gram |
| Oil of spearmint | 0.3 | gram |
| Oil of cassia | 0.3 | gram |
| Saccharin | 0.5 | gram |
| Strontium edatate | 10 | grams |
| Tincture cudbear | 0.6 | gram |
| Water quantity sufficient to make | 100 | cc |

The alcohol and glycerine are added to one another and stirred together, and, the ricinoleate then is dissolved in the alcohol and glycerine solution. The saccharin then is stirred in and also the tincture cudbear for coloring. Then the strontium edatate (crystalline) is stirred in and followed by the flavoring ingredients, namely, the oils of cloves, spearmint, and cassia; and finally the water is added, and the whole is stirred to uniformity.

The toothpastes of Examples 1–6 are utilized following a regular daily routine preferably twice a day. The liquid dentifrice of Example 7 is preferably used as a mouthwash and can be diluted in water, as with any ordinary mouthwash, and preferably is used at least twice a day.

I claim:

1. A water-containing dentifrice consisting essentially of strontium edatate in an amount sufficient to provide from about 2.5 wt.% to about 25 wt.% of strontium ion and from about 0.1 wt.% to about 10 wt.% of a ricinoleate compound said dentifrice being free from strontium edatate-sequestering Ca, Mg, Al, Sn metal.

2. A dentifrice according to claim 1 in which the ricinoleate is sodium ricinoleate.

3. A method for controlling calculus which comprises applying to the teeth a water-containing dentifrice consisting essentially of strontium edatate in an amount sufficient to provide from about 2.5 wt.% to about 25 wt.% of strontium ion and about 0.1 wt.% to about 10 wt.% of a ricinoleate said dentifrice being free from strontium edatate-sequestering Ca, Mg, Al, Sn metal.

* * * * *